(12) United States Patent  
Maida

(10) Patent No.: US 6,452,999 B1  
(45) Date of Patent: Sep. 17, 2002

(54) CRADLE FOR X-RAY CT SYSTEM AND X-RAY CT SYSTEM

(75) Inventor: Masashi Maida, Tokyo (JP)

(73) Assignee: GE Medical Systems Global Technology Company, LLC, Waukesha, WI (US)

(\*) Notice: Subject to any disclaimer, the term of this patent is extended or adjusted under 35 U.S.C. 154(b) by 85 days.

(21) Appl. No.: 09/770,043

(22) Filed: Jan. 25, 2001

(30) Foreign Application Priority Data

Feb. 28, 2000 (JP) .................................. 2000-051837

(51) Int. Cl.$^7$ ................................................ A61B 6/00
(52) U.S. Cl. ........................ 378/20; 378/208; 378/209
(58) Field of Search ............................ 378/20, 4, 208, 378/209, 601, 690, 902

(56) References Cited

U.S. PATENT DOCUMENTS

| | | | | |
|---|---|---|---|---|
| 4,727,328 A | * | 2/1988 | Carper et al. | ............... 324/318 |
| 5,555,284 A | * | 9/1996 | Kishigami | .................. 378/177 |
| 5,600,858 A | * | 2/1997 | Baer | ........................... 378/209 |
| 5,619,763 A | * | 4/1997 | Randolph et al. | ............ 378/209 |

\* cited by examiner

*Primary Examiner*—David V. Bruce  
*Assistant Examiner*—Pamela R. Hobden  
(74) *Attorney, Agent, or Firm*—Moonray Kojima

(57) ABSTRACT

In order to reduce artifacts entering an X-ray tomographic image of a subject in performing a scan at an end portion of a cradle, and offer a reliable diagnosis environment, the cradle has a top surface forming a concave curve as viewed from the front, and has a generally bowl-like shape in a cross section as viewed from the carrying direction. The cradle further has a shape at its end portion which, when points at the same position with respect to the carrying direction on two peripheries along which the top surface and two lateral sides abut are represented as Points A and B, and a point at the center position on a minimal curve connecting Points A and B is represented as Point C, is cut in a plane passing through Points A and C, and through a Point F for descending the plane in a direction opposite to the carrying direction, and which is cut in a plane passing through Points B and C, and through a Point G for descending the plane in a direction opposite to the carrying direction.

20 Claims, 11 Drawing Sheets

CRADLE FOR X-RAY CT SYSTEM AND X-RAY CT SYSTEM

BACKGROUND OF THE INVENTION

The present invention relates to a cradle for supporting a subject (human subject) in an X-ray CT system that obtains an X-ray tomographic image of the subject by means of X-ray exposure.

An X-ray CT (computerized tomography) system and apparatus comprises an apparatus (generally referred to as a gantry apparatus) having a toroidal cavity portion therein, and an operating console for supplying several types of control signals to the gantry apparatus and reconstructing an X-ray tomographic image for display based on signals (data) acquired by the gantry apparatus.

The gantry apparatus has an X-ray source (X-ray tube), an X-ray detector for detecting X-rays, and a cavity for disposing a subject therebetween. By rotating the X-ray source and X-ray detector, signals (data) are obtained at different rotation angles corresponding to the amount of X-rays which has passed through (and been attenuated by) the subject. In response to the signals, the operating console arithmetically calculates the X-ray attenuation factor in a small portion in a cross-sectional plane through the subject, and displays the calculated value as a pixel value to ultimately create an image visible by a human observer. The image is generally referred to as an X-ray tomographic image, and the process of creating the X-ray tomographic image is referred to as an X-ray tomographic image reconstruction process, or more simply, as reconstruction.

In addition to the above components, the X-ray CT system requires a carrier apparatus for supporting and immobilizing the subject in the cavity portion in the gantry apparatus and for carrying the subject toward the cavity portion. A table which is provided over the carrier apparatus and with which the subject comes in direct contact generally referred to as a cradle.

Since the cradle, along with the subject, is exposed to X-rays, the material constituting the cradle is required to have a high transmission factor to X-rays. In general, a material comprising a foam material, such as acrylic resin, reinforced by a surrounding CFRP (carbon fiber-reinforced plastic) or the like is employed.

In the X-ray CT system, noise images, referred to as artifacts, sometimes appear on a reconstructed image. An artifact occurs when an object has a higher X-ray attenuation factor (a lower X-ray transmission factor) than its surroundings. If the noise occurs outside the reconstructed X-ray tomographic image of a subject, it causes no problem. However, a noise occurring inside the reconstructed image may lead to misdiagnosis.

It is also known that the artifact phenomenon is pronounced in the tangential direction of an object having a high X-ray attenuation factor.

The relationship between a conventional cradle configuration and artifacts will now be described.

FIG. 1 shows three-direction projection views of a cradle around its end portion on a side near the gantry apparatus, in which (a) is a top plan view of the cradle (a view from upside of a subject, if placed on the cradle), (b) is a front (end) view from the carrying direction (i.e., from the gantry apparatus), and (c) is a side view.

As shown, the cross section of the cradle as viewed from the cross section or from the carrying direction has a bowl-like shape (inverted trapezoidal shape) whose top periphery forms a concave curve, as shown in the end view (b), so that the lying subject is stably supported. Moreover, the cross section as viewed from the lateral side is formed as a shape cut at an end at an angle θ, as shown in the side view (c). (The reason for the cut shape will be described later.)

FIG. 2 shows an exemplary X-ray tomographic image reconstructed by laying a subject on the illustrated cradle and scanning the subject at a position S shown in FIG. 1. (The scan plane is orthogonal to the drawing plane of FIG. 1.)

Although the cradle is made from a material with a high X-ray transmission factor, the reinforcing CFRP constituting the surface of the cradle has a lower transmission factor than the ambient air. Accordingly, many linear artifacts are generated along the tangential direction of the CFRP covering the surface, as shown in FIG. 2.

Since the cross section of the cradle has a bowl-like shape, the artifacts generated at the lateral surfaces of the cradle appear only in a direction away from the subject. Similarly, the artifacts generated at the curved surface on which the subject is placed appear only in the tangential direction and do not enter the X-ray tomographic image of the subject. In these points, it may safely be said that these artifacts substantially do not affect a diagnosis based on the X-ray tomographic image in such a condition as shown in FIG. 2.

Next, the reason for the shape of the end portion cut at an angle of θ as viewed from the lateral side shown in FIG. 1 will be explained, and then problems about artifacts at the end portion will be discussed.

A principal cause of artifacts is the existence of a material with a low X-ray transmission factor in a scan plane. Therefore, if the end surface of the cradle is not slanted but, unlike that shown in FIG. 1, is perpendicular, artifacts are generated when a position that coincides with the perpendicular end surface is scanned, because a CFRP layer having a low X-ray transmission factor extends in a plane that coincides with the scan plane. Hence, the surface at the end portion of the cradle is made slanted as shown in the side view FIG. 1(c).

The angle θ should be larger than a certain value. This is because a scan may possibly be performed with the gantry apparatus tilted by a certain angle θ0, rather than always being performed in a plane orthogonal to the carrying direction of the cradle, as shown in FIG. 3. The tilt is made because, for example, a range of vertebrae constituting the backbone of a human subject extends in a gentle S-shaped curve and an X-ray tomographic image sometimes needs to be reconstructed in a plane orthogonal to a certain portion in such a curved range. Therefore, if the slope angle θ at the end portion of the cradle is smaller than the maximum tilt angle, there occurs a situation in which the tilt angle of the gantry is equal to θ in an actual use, causing those artifacts described above to be generated. Hence, the slope angle θ of the end surface of the cradle is required to be larger than the maximum tilt angle of the gantry apparatus. However, if the gantry apparatus does not have a tilt function, a moderate angle will do without the above limitation on the angle.

Moreover, when a subject is laid on the cradle, the end portion may support either the head or the feet of the subject. Since a scan requires a stable condition of the subject, some cradles include a mechanism at the end portion for stably securing the head of the subject. This is achieved by inserting a head rest into an attachment slot provided at the end surface of the cradle, as shown in FIG. 4.

Consider a case of performing a scan at a position, designated by reference symbol S in FIG. 5, in the carrying direction (generally referred to as the Z-axis).

In the illustrated case, a scan plane intersects two portions Pa and Pb at the corners of the cradle. The cross section of the scan plane is shown at "S-cross section" in FIG. 5, and two end cross sections Pa and Pb of the cradle are formed.

As can also be seen from the enlarged view of the cross sections Pa and Pb of the end portion of the cradle, bottom peripheries Pa1 and Pb1 of these cross sections (which are in a layer of CFRP) are both horizontal, and in addition, are collinear. Consequently, artifacts are generated, or tend to be generated, on a line connecting the bottom peripheries Pa1 and Pb1. Therefore, if a certain site of the subject is placed at the end portion of the cradle, the artifact connecting the bottom peripheries Pa1 and Pb1 enters the X-ray tomographic image, as shown in FIG. 5, preventing an accurate diagnosis.

SUMMARY OF THE INVENTION

The present invention was made in consideration of such problems, and is directed to providing a cradle and an X-ray CT system for reducing artifacts entering an X-ray tomographic image of a subject in performing a scan at an end portion of the cradle, and offering a reliable diagnosis environment.

In order to solve such problems, a cradle for an X-ray CT system of the present invention has, in one embodiment, the following configuration:

- a cradle for placing thereon a subject in an X-ray CT system and for carrying the subject toward a scan position:
    - which has a top surface for placing the subject thereon that forms a concave curve as viewed from the carrying direction;
    - which has a generally bowl-like shape in a cross section as viewed from the carrying direction; and
    - representing points at the same position with respect to the carrying direction on two peripheries along which the top surface and two lateral surfaces abut as A and B, and n points on a minimal curve connecting Points A and B on the top surface as $C1, \ldots, Cn$,
    - which has at an end portion a shape that is cut in a plane passing through Points A and C1 and descending toward a direction opposite to the carrying direction, is cut in a plane passing through Points Ci and Ci+1 and descending toward a direction opposite to the carrying direction, and is cut in a plane passing through Points B and Cn and descending toward a direction opposite to the carrying direction.

According to the present invention as described above, artifacts entering an X-ray tomographic image of a subject can be reduced in performing a scan at an end portion of a cradle, and a reliable diagnosis environment can be offered.

Further objects and advantages of the present invention will be apparent from the following description of the preferred embodiments of the invention as illustrated in the accompanying drawings.

DETAILED DESCRIPTION OF THE INVENTION

Embodiments in accordance with the present invention will now be described in detail with reference to the accompanying drawings.

Figure 6:
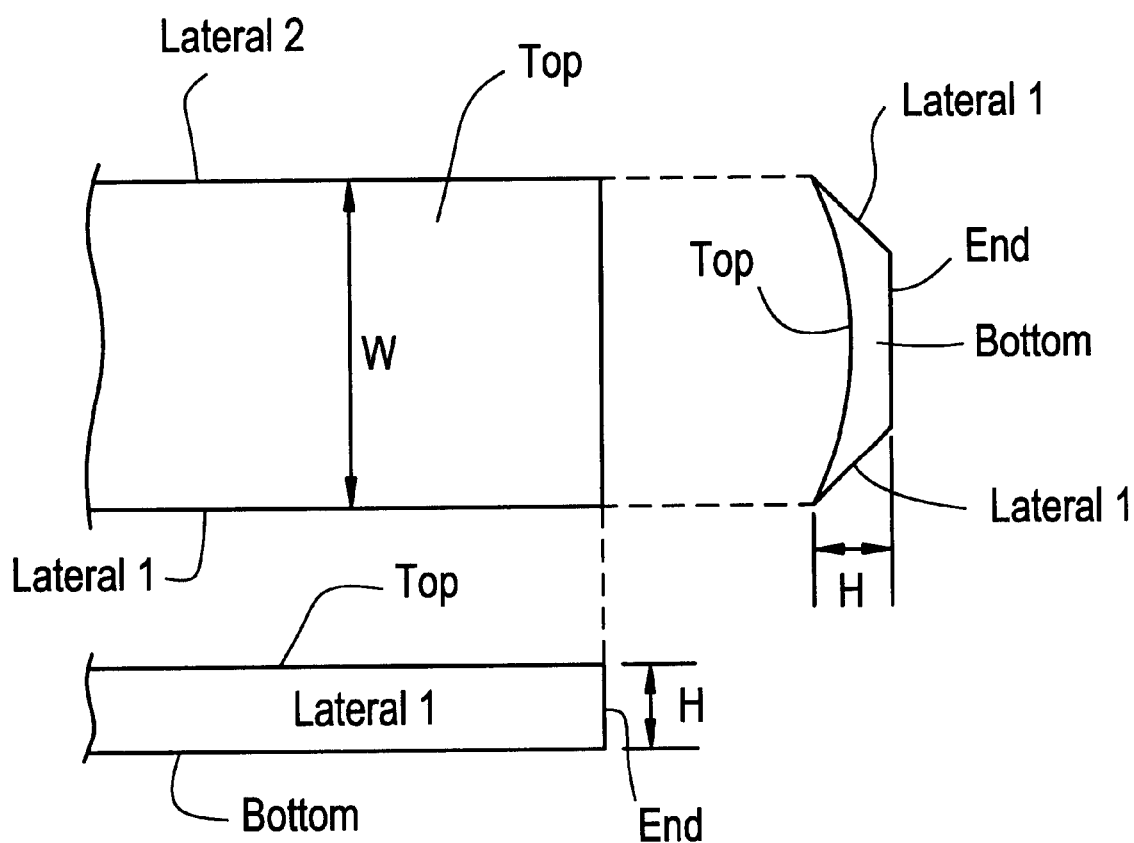
FIG. 6 illustrates an end portion of a cradle blank from which a cradle that is a first embodiment of the present invention is made.

For convenience in appreciating the shape of a cradle according to a first embodiment, consider a cradle blank from which the cradle is made, having the shape shown in FIG. 6. The illustrated blank has a width W and a height H, and surfaces of the blank will be represented by the designations in FIG. 6 hereinbelow.

Figure 7:
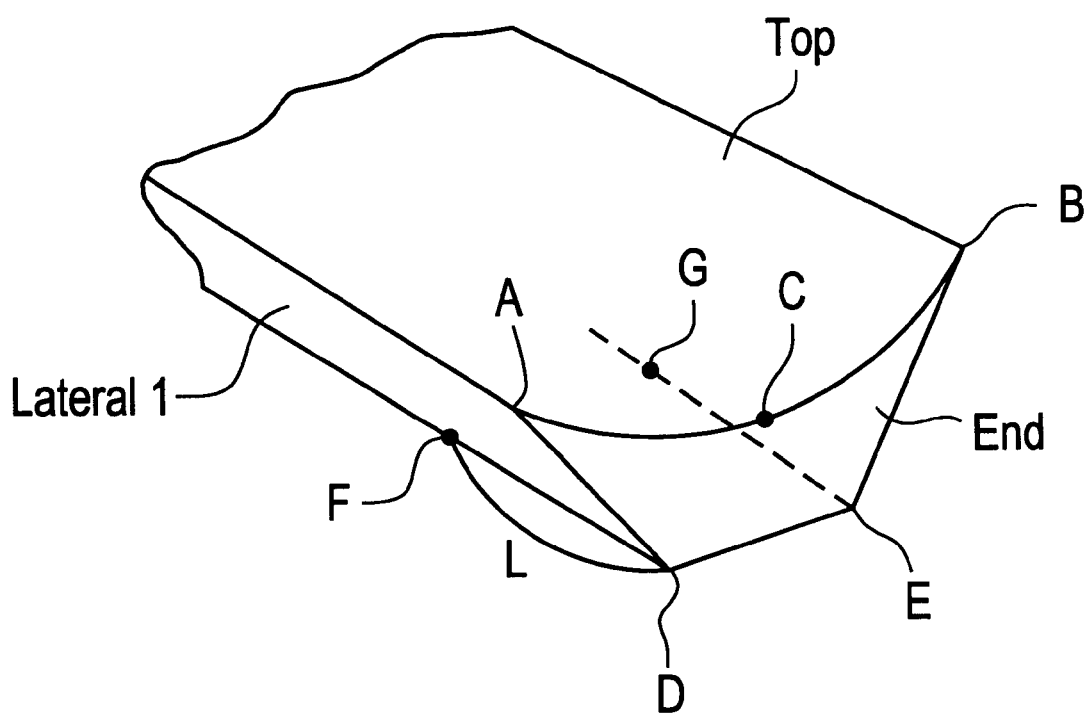
FIG. 7 is an exterior perspective view of the end portion of the blank shown in FIG. 6.

In FIG. 6, the shape of the blank as viewed from the carrying direction is the same as that shown in the front view of FIG. 1(b). However, the end surface at this stage is orthogonal to the bottom surface (has not yet been angled). FIG. 7 is a perspective view of the blank.

Points A–G shown in FIG. 7 are defined as follows:

Points A, B: Two corners on the top surface of the blank. These points are at the same position with respect to the carrying direction (generally referred to as the Z-axis);

Point C: A center position on a curved periphery connecting the top and end surfaces of the blank (a center on a minimal curve connecting Points A and B on the top surface);

Points D, E: Two corners on the bottom surface of the blank;

Point F: A point on a periphery connecting the bottom surface and a lateral surface 1 of the blank at a distance L from Point D; and Point G: A point on a periphery connecting the bottom surface and a lateral surface 2 (not visible in FIG. 7) of the blank at a distance L from Point E;

The so-defined Points A, C and F define a plane (which is a plane descending toward a direction opposite to the carrying direction). Points B, C and G define another similar plane. The shape of the end portion of the cradle in the present embodiment is formed by cutting the blank in these two planes.

Figure 8:
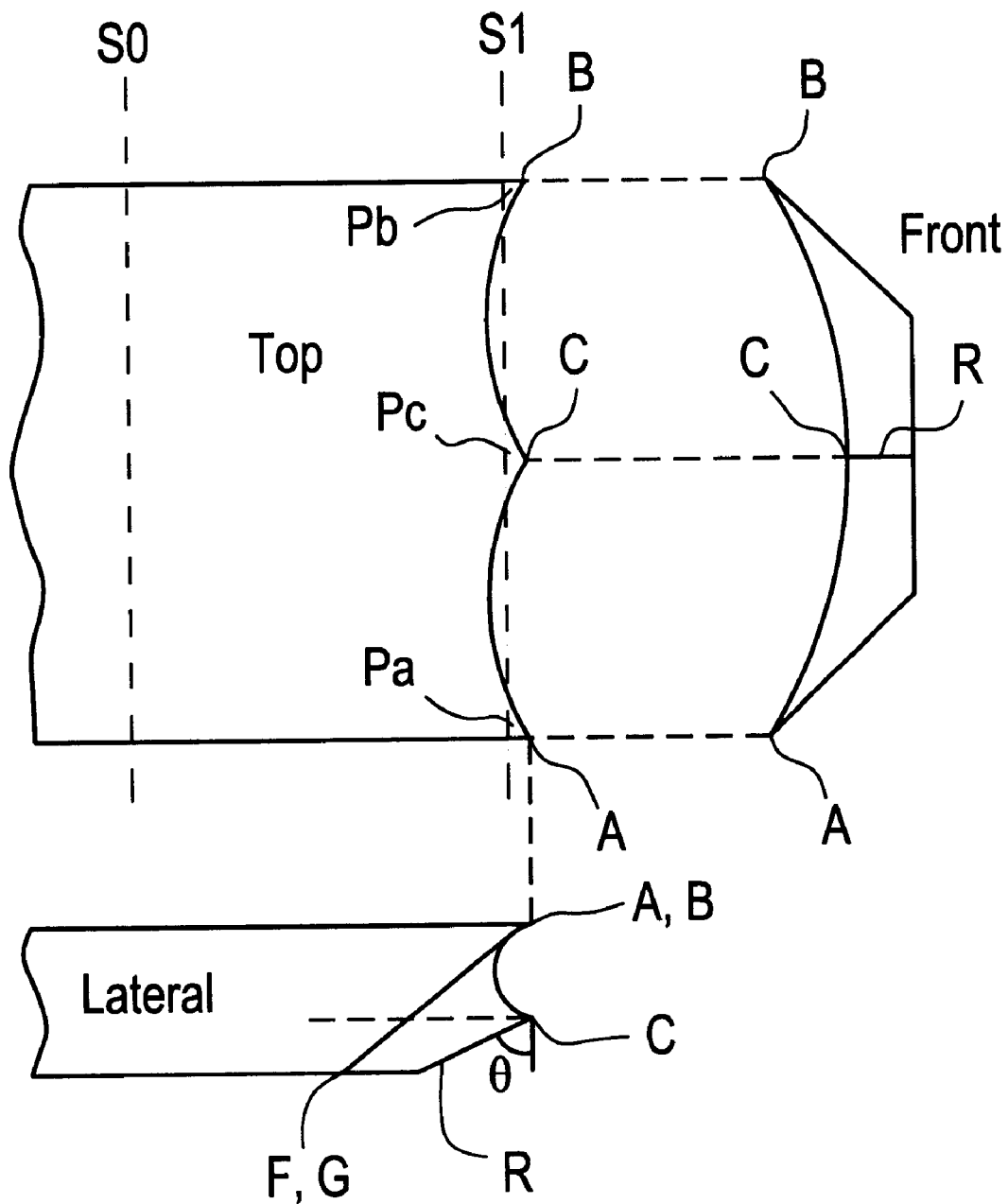
FIG. 8 illustrates the shape of the end portion of the cradle in the first embodiment.

FIG. 8 shows three-direction projection views of the shape of the end portion of the cradle in the present embodiment. In FIG. 8, reference numerals A–C and F and G are the same as those shown in FIG. 7.

Figure 1:
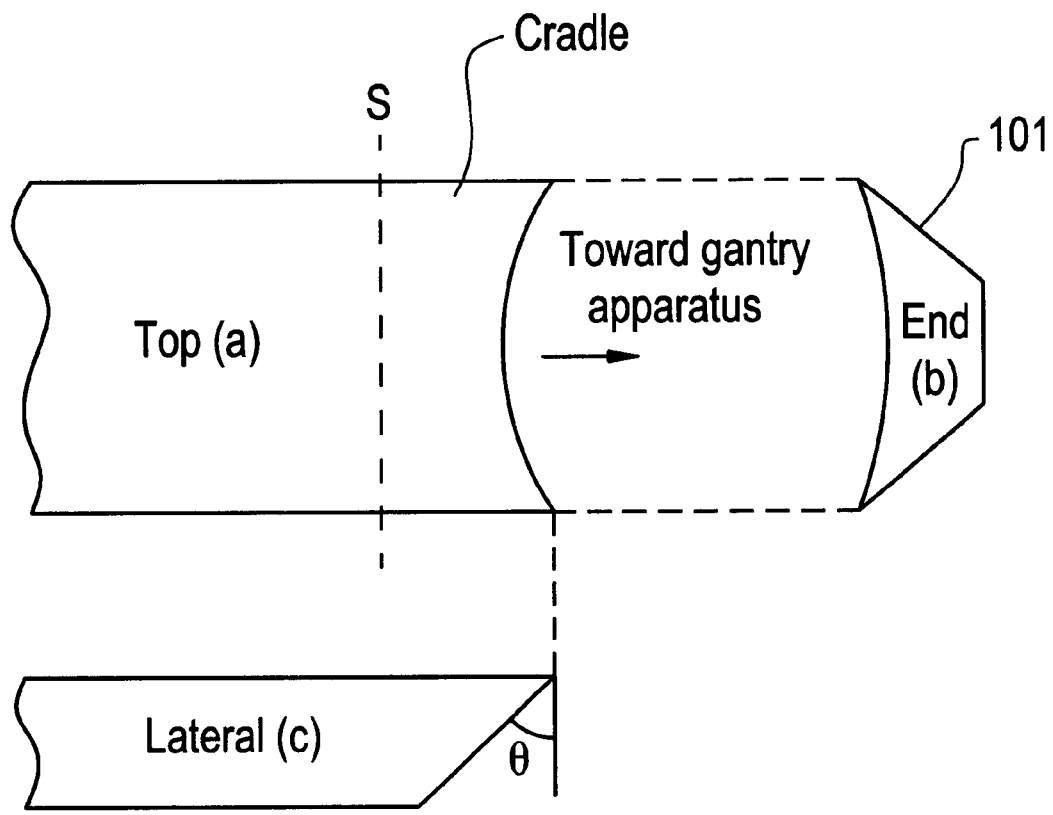
FIG. 1 illustrates a shape at an end portion of a conventional cradle.

It should be noted that the distance L may be set such that an angle θ of a ridgeline R between the two cut surfaces with respect to the vertical surface is θ shown in FIG. 1. The significance of the angle θ was explained earlier and will not be repeated here.

Figure 2:
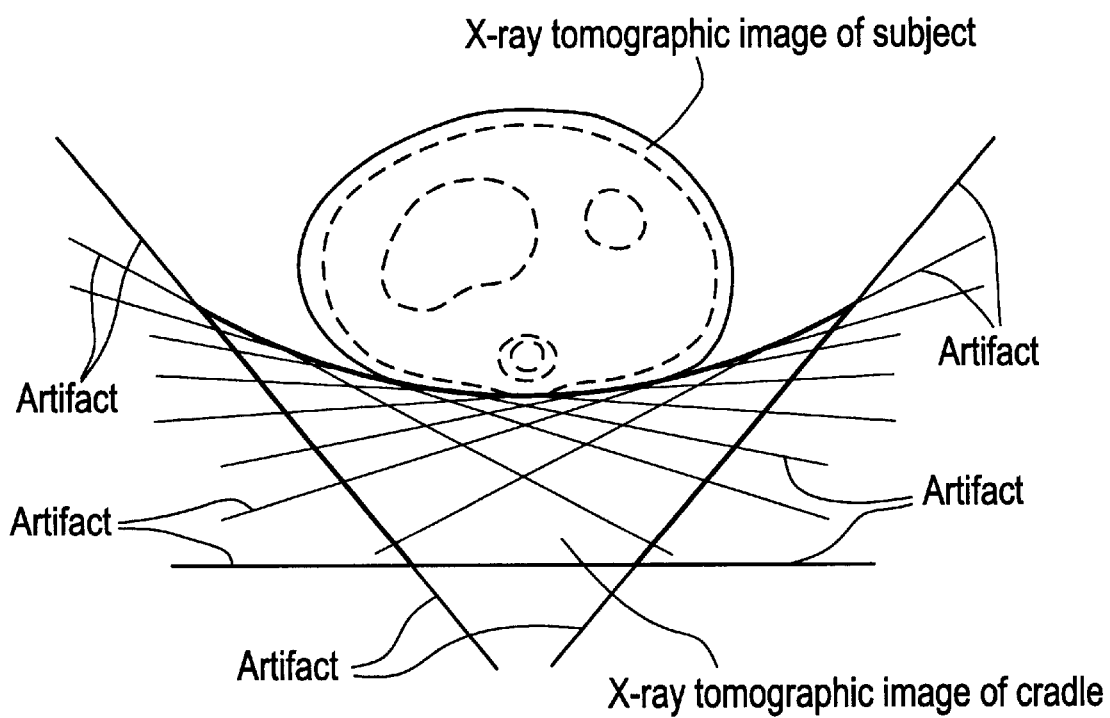
FIG. 2 illustrates a relationship between an X-ray tomographic image and artifacts at a position S in FIG. 1.
Figure 3:
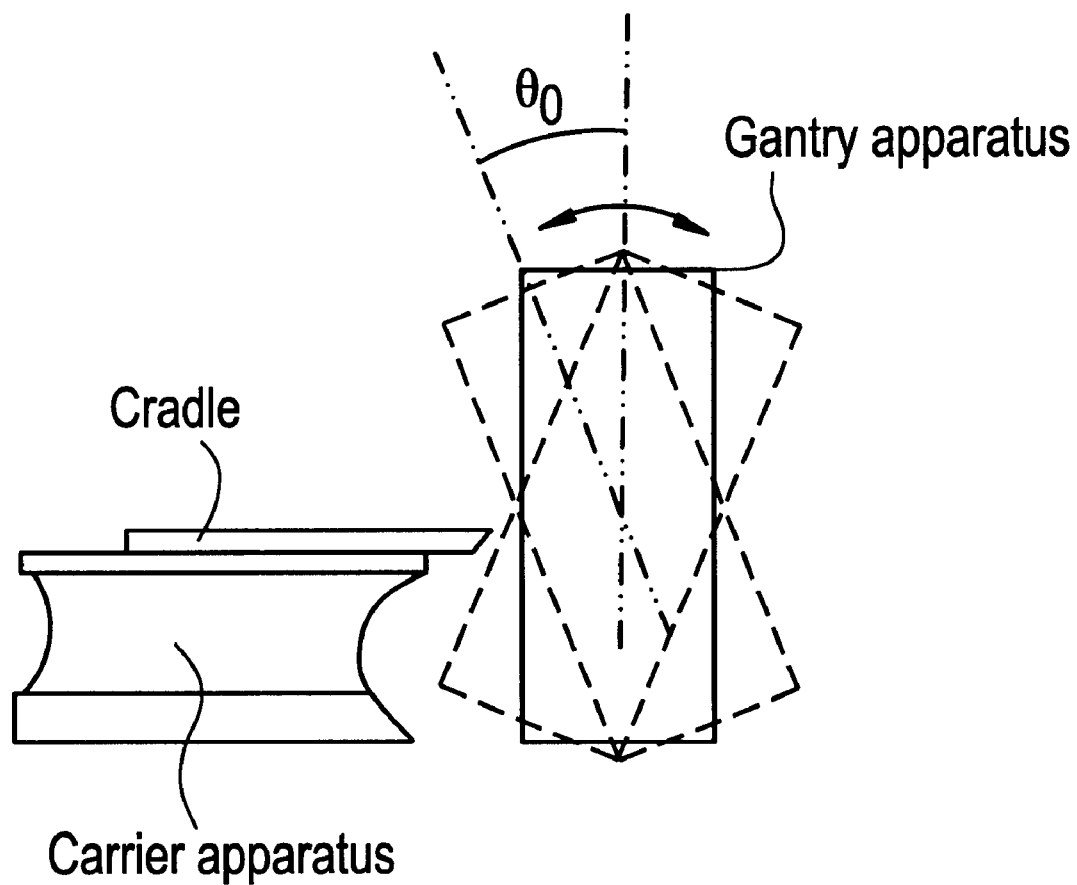
FIG. 3 is a view for explaining a tilting operation of a gantry apparatus.

An X-ray tomographic image reconstructed by performing a scan at a position S0 with respect to the carrying direction offers the same result as in the image at the position S in FIG. 1 described before, and artifacts which are generated or tend to be generated are the same as those shown in FIG. 2. Therefore, explanation thereof will not be repeated.

An explanation will be made for the case of performing a scan at a position S1 in FIG. 8. The scan plane (a plane perpendicular to the drawing plane) at the scan position S1 intersects three portions Pa, Pb and Pc of the cradle, as shown in FIG. 8.

Figure 9:
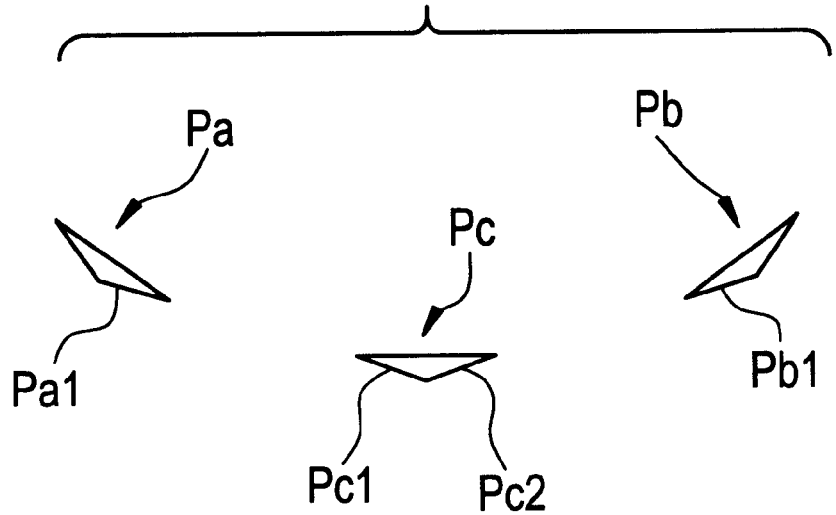
FIG. 9 is a cross-sectional view in performing a scan at the end portion of the cradle in the first embodiment.

FIG. 9 shows the respective tomographic images of the portions Pa, Pb and Pc when a scan is performed at the position S0. Each of the portions Pa, Pb and Pc has a generally triangular shape as shown (though strictly speaking, the top periphery of each triangle is curved), and the fact that the bottom periphery Pa1 of the portion Pa and the bottom periphery Pc1 of the portion Pc are collinear should be noted. The reason for the collinearity is that the peripheries Pa1 and Pc1 are both on an intersection line between the plane defined by Points A, C and F described with reference to FIG. 7 and the scan plane at S1 in FIG. 8, i.e., on an intersection line between two planes. Similarly, the bottom periphery Pb1 of the portion Pb and the bottom periphery Pc2 of the portion Pc are collinear.

Figure 10:
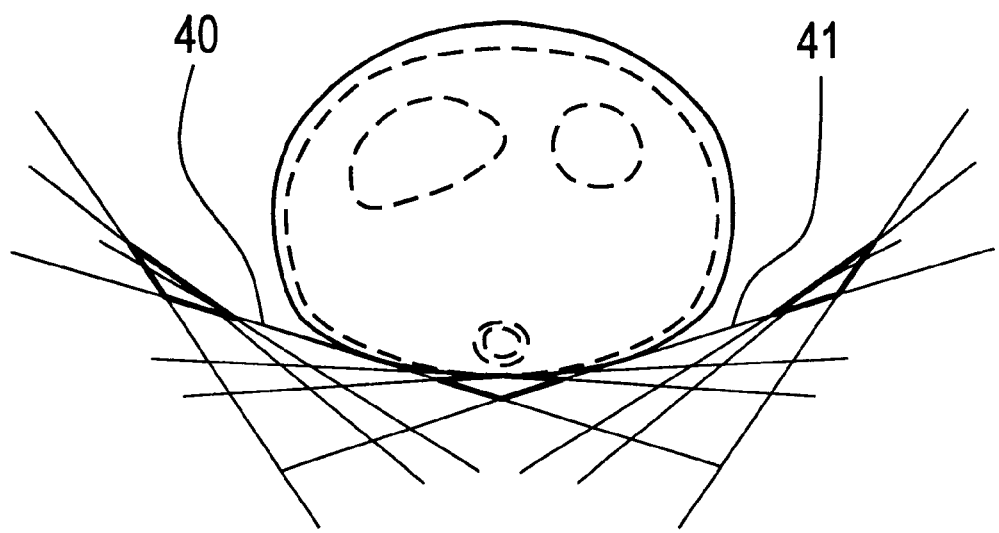
FIG. 10 illustrates artifacts in performing a scan at the end portion of the cradle in the first embodiment.

Accordingly, an X-ray tomographic image reconstructed, and artifacts which are generated or tend to be generated, by actually laying a subject on the cradle configured as above and performing a scan at the position S1 will be those shown in FIG. 10.

As shown, although several causes for generating artifacts are present, those which are generated nearest to the X-ray tomographic image of the subject are artifacts 40 and 41 shown in FIG. 10. It will be easily recognized that the artifacts 40 and 41 are a line connecting the peripheries Pa1 and Pc1 and a line connecting the peripheries Pb1 and Pc2, respectively, shown in FIG. 9.

Figure 5:
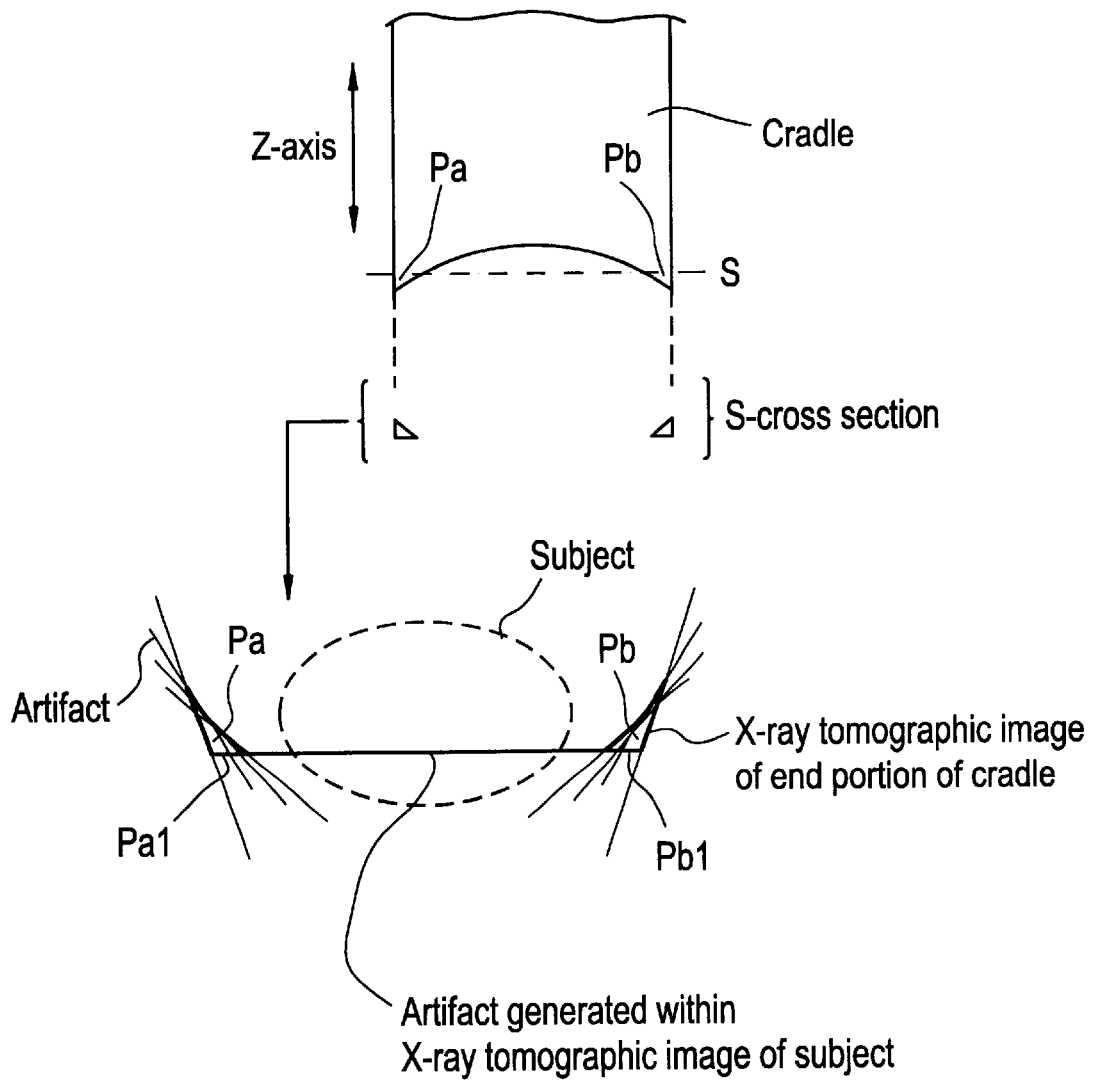
FIG. 5 illustrates a relationship between an X-ray tomographic image and artifacts in performing a scan at the end portion of the cradle shown in FIG. 1.

Comparing FIGS. 10 and 5, it will be appreciated that artifacts entering the X-ray tomographic image of the subject are successfully and markedly reduced when a scan is performed near the end portion of the cradle of the present embodiment.

Therefore, when an X-ray tomographic image is reconstructed at an end portion of a cradle, the shape of the end portion of the cradle of the present embodiment can reduce artifacts entering the X-ray tomographic image of the subject, and a highly reliable X-ray tomographic image can be reconstructed throughout the length of the cradle.

Figure 4:
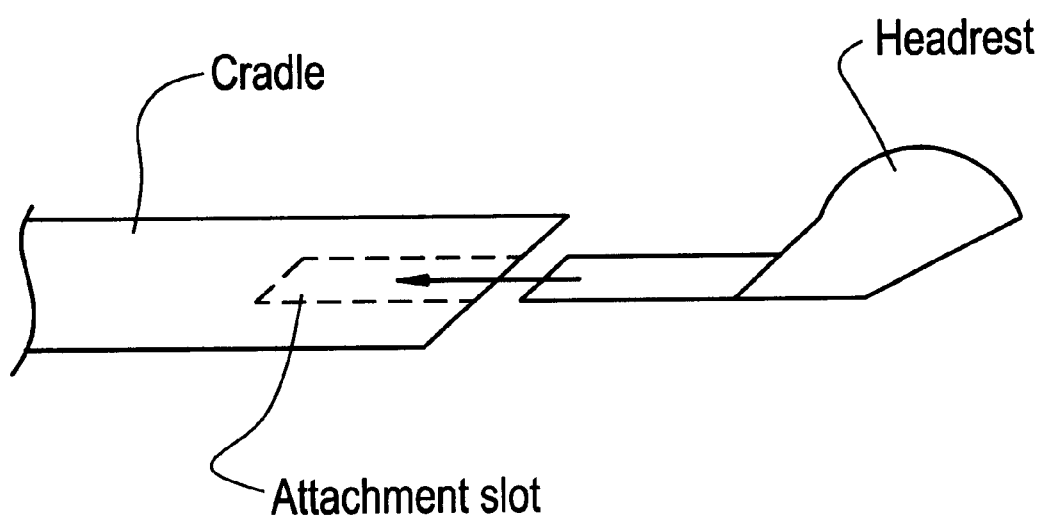
FIG. 4 illustrates how a head rest is attached to a cradle.

It should be noted that the cradle described according to this embodiment can be provided with an attachment slot for connecting the head rest as shown in FIG. 4. It is desirable that the shape of the slot be one for suppressing artifacts entering the X-ray tomographic image of the subject. The slot may simply have a cross-sectional shape homothetic to that of the cradle. In this case, the surface of the head rest abutting against the cradle may be formed in a shape that closely contacts the end surface of the cradle so as to reduce artifacts entering the X-ray tomographic image of the subject, even if artifacts are generated by the end surface of the head rest.

Second Embodiment

The above embodiment has a shape obtained by cutting the cradle blank as shown in FIG. 6 in two planes. However, two artifacts lines 40 and 41 nearest to the X-ray tomographic image of the subject shown in FIG. 10 lie above the curved top surface of the cradle at a very small distance, i.e., enter the X-ray tomographic image of the subject.

Reduction of the amount of entry can be achieved by a shape obtained by cutting the blank shown in FIG. 6 in three planes or more.

A case of cutting the member in three planes will therefore be described as a second embodiment hereinbelow.

Figure 11:
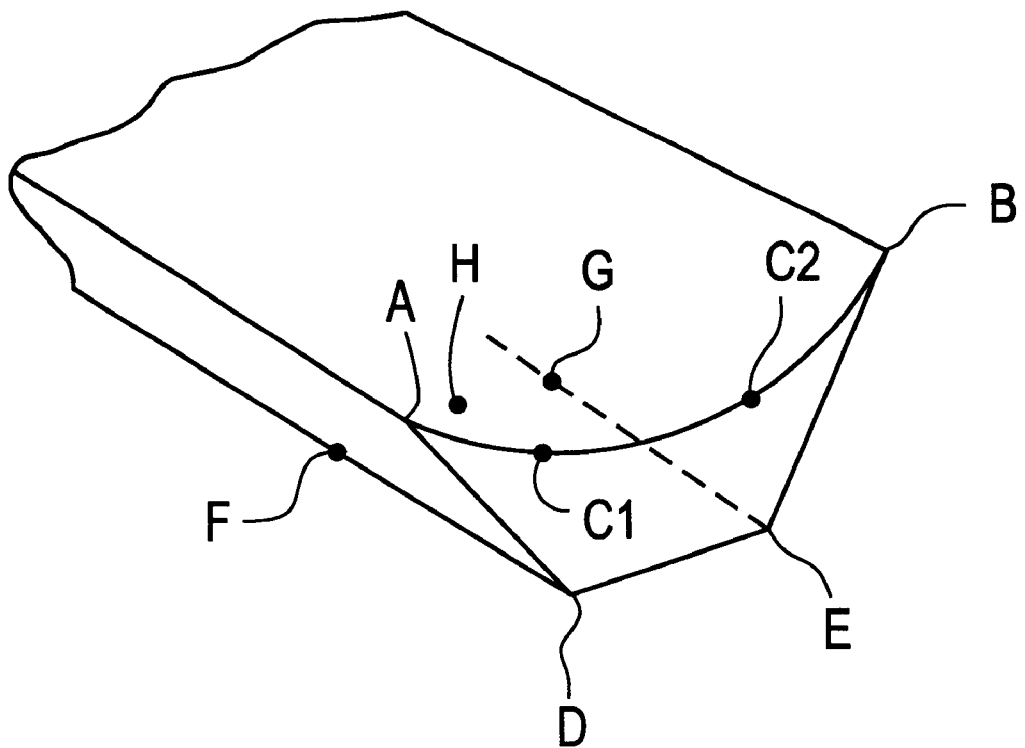
FIG. 11 is an exterior perspective view of a cradle blank for defining the shape of an end portion of a cradle that is a second embodiment.

To define the cutting positions, FIG. 11 illustrates these positions for the blank shown in FIG. 6.

In. FIG. 11, Points A, B and D–G are the same as those shown in FIG. 7, and explanation thereof will be omitted. Points C1, C2 and H are defined as follows:

Points C1 and C2: Equally trisected positions on a curve connecting the top and end surfaces (i.e., positions equally trisecting a minimal curve connecting Points A and B on the top surface); and Point H: A midpoint of a line connecting Points F and G on the bottom surface.

According to the second embodiment, the blank is cut in a surface defined by Points A, C1, and F, a plane defined by Points C1, C2 and H and a plane defined by Points B, C2 and G. The shape after cutting forms the end portion of the cradle in the second embodiment.

Figure 12:
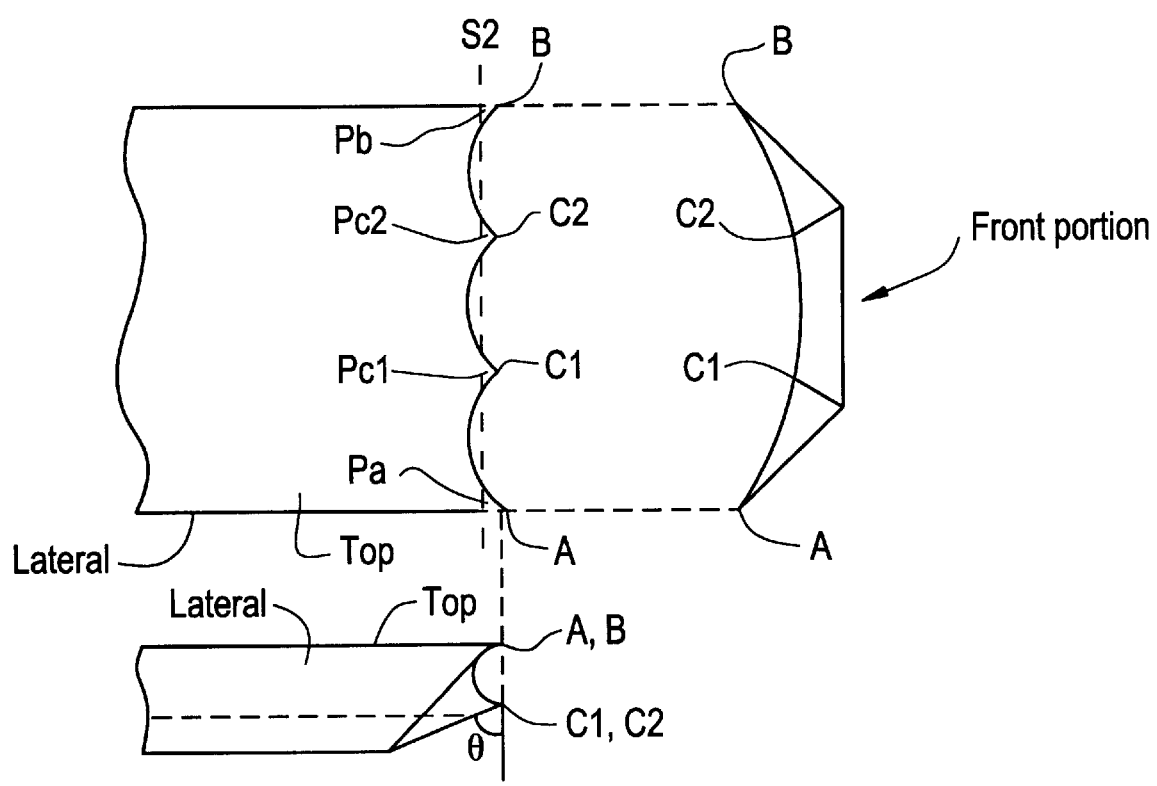
FIG. 12 illustrates the shape of the end portion of the cradle in the second embodiment.

FIG. 12 shows three-direction projection views of the cradle in accordance with the second embodiment. It should be noted that Point H is not necessarily the midpoint on a line connecting Points F and G, and it may lie nearer to the periphery DE. The essential thing is to assuredly maintain the angle $\theta$ of the end surface with respect to the vertical plane.

When a scan is performed at a position S2 in FIG. 12, four end portions of the cradle Pa, Pc1, Pc2 and Pb are intersected, as shown in FIG. 12. As can be easily seen from the front elevation in FIG. 12, what is meant by the four portions is exactly that the number of divisions on the curve along the top surface of the cradle is increased by one relative to that shown in FIG. 9. It will be easily recognized by those skilled in the art that a line connecting the four bottom peripheries of those portions serve to approximate a curved surface more accurately. The reason is the same as why a regular polygon having N+1 sides approximates a circle more accurately than one with N sides. Thus, artifacts generated also come closer to the curved top surface, extending in a direction away from the X-ray tomographic image of the subject.

According to the second embodiment as described above, the number of artifacts entering an X-ray tomographic image of a subject can be reduced more than in the cradle of the first embodiment.

Moreover, although Points C, C1 and C2 on a minimal curve connecting Points A and B on the top surface are described as dividing the curve into equal portions with reference to FIGS. 7 and 11, these points are not limited thereto, and the number of the points is not limited to one or two but may be more.

Many widely different embodiments of the invention may be configured without departing from the spirit and the scope of the present invention. It should be understood that the present invention is not limited to the specific embodiments described in the specification, except as defined in the appended claims.

What is claimed is:

1. A cradle for holding and carrying a subject toward a scanning position in an X-ray CT system, said cradle comprising:

a top surface for holding said subject, said top surface forming a concave curve as viewed from a carrying direction;

a generally bowl-like shape in a cross section as viewed from said carrying direction; and representing points at a same position with respect to said carrying direction on two peripheries along which said top surface and two lateral surfaces abut as A and B, and $\underline{n}$ points on a minimum curve connecting points A and B on said top surface as C1, ..., Cn; wherein said cradle further comprises:

an end portion thereof having a shape that (a) is cut in a plane passing through Points A and C1 and descending toward a direction opposite to said carrying direction, (b) is cut in a plane passing through Points Ci and Ci+1 and descending toward a direction opposite to said carrying direction, and (c) is cut in a plane passing through Points B and Cn and descending toward a direction opposite to said carrying direction.

2. The cradle of claim 1, wherein number of said points on said minimum curve connecting Points A and B is one.

3. The cradle of claim 1, wherein number of said points on said,minimum curve connecting Points A and B is two.

4. The cradle of claim 1, further comprising a head rest portion attached to a surface of a side of said cradle having a generally bowl-like shape in said carrying direction.

5. The cradle of claim 4, wherein said head rest portion comprises an attachment surface having a shape which fits said surface having a generally bowl-like shape.

6. The cradle of claim 4, wherein said head rest portion has a top surface formed of a concave curve as viewed from said carrying direction.

7. The cradle of claim 5, wherein said attachment surface of said head rest portion is provided with a protruding portion; and wherein an attaching surface of said cradle facing said head rest portion is provided with a slot for receiving said protruding portion.

8. The cradle of claim 7, wherein said slot has a cross-sectional shape homothetic to a cross sectional shape of said cradle.

9. The cradle of claim 1, wherein said cradle is formed of a foam material enclosed by carbon fiber reinforced plastic.

10. The cradle of claim 9, wherein said foam material is acrylic resin.

11. An X-ray CT system comprising a cradle for holding and carrying a subject toward a scanning position, said cradle comprising:

a top surface for holding said subject, said top surface forming a concave curve as viewed from a carrying direction;

a generally bowl-like shape in a cross section as viewed from said carrying direction; and representing points at a same position with respect to said carrying direction on two peripheries along which said top surface and two lateral surfaces abut as A and B, and $\underline{n}$ points on a minimum curve connecting points A and B on said top surface as C1, ..., Cn; wherein said cradle further comprises:

an end portion thereof having a shape that (a) is cut in a plane passing through Points A and C1 and descending toward a direction opposite to said carrying direction, (b) is cut in a plane passing through Points Ci and Ci+1 and descending toward a direction opposite to said carrying direction, and (c) is cut in a plane passing through Points B and Cn and descending toward a direction opposite to said carrying direction.

12. The system of claim 11, wherein number of said points on said minimum curve connecting Points A and B is one.

13. The system of claim 11, wherein number of said points on said minimum curve connecting Points And an B is two.

14. The system of claim 11, further comprising a head rest portion attached to a surface of a side of said cradle having a generally bowl-like shape in said carrying direction.

15. The system of claim 14, wherein said head rest portion comprises an attachment surface having a shape which fits said surface having a generally bowl-like shape.

16. The system of claim 14, wherein said head rest portion has a top surface formed of a concave curve as viewed from said carrying direction.

17. The system of claim 15, wherein said attachment surface of said head rest portion is provided with a protruding portion; and wherein an attaching surface of said cradle facing said head rest portion is provided with a slot for receiving said protruding portion.

18. The system of claim 17, wherein said slot has a cross-sectional shape similar to the cross sectional shape of said cradle.

19. The system of claim 11, wherein said cradle is formed of a foam material enclosed by carbon fiber reinforced plastic.

20. The system of claim 19, wherein said foam material is acrylic resin.

* * * * *